US011331514B2

(12) United States Patent
Tortora

(10) Patent No.: US 11,331,514 B2
(45) Date of Patent: May 17, 2022

(54) INGESTIBLE CAPSULE FOR THE PHOTOTHERAPEUTIC TREATMENT OF INFECTIONS

(71) Applicant: PROBIOMEDICA S.R.L., Florence (IT)

(72) Inventor: Giuseppe Roberto Tortora, Pisa (IT)

(73) Assignee: PROBIOMEDICA S.R.L., Florence (IT)

( * ) Notice: Subject to any disclaimer, the term of this patent is extended or adjusted under 35 U.S.C. 154(b) by 165 days.

(21) Appl. No.: 16/472,096

(22) PCT Filed: Dec. 20, 2017

(86) PCT No.: PCT/IB2017/058227
§ 371 (c)(1),
(2) Date: Jun. 20, 2019

(87) PCT Pub. No.: WO2018/116216
PCT Pub. Date: Jun. 28, 2018

(65) Prior Publication Data
US 2020/0114171 A1 Apr. 16, 2020

(30) Foreign Application Priority Data

Dec. 21, 2016 (IT) .......................... 102016000129679

(51) Int. Cl.
*A61N 5/06* (2006.01)
(52) U.S. Cl.
CPC ......... *A61N 5/0624* (2013.01); *A61N 5/0603* (2013.01); *A61N 2005/0609* (2013.01);
(Continued)
(58) Field of Classification Search
CPC .. A61N 5/0601; A61N 5/0603; A61N 5/0624; A61N 2005/0609;
(Continued)

(56) References Cited

U.S. PATENT DOCUMENTS 5,728,090 A * 3/1998 Martin ................ A61N 5/0601
606/11
6,159,236 A * 12/2000 Biel ...................... A61M 25/10
604/20
(Continued)

FOREIGN PATENT DOCUMENTS

| CN | 203935519 U | 11/2014 |
| WO | WO 2011/055395 A1 | 5/2011 |
| WO | WO 2012/123939 A1 | 9/2012 |

OTHER PUBLICATIONS

International Search Report and Written Opinion of the International Searching Authority dated Apr. 3, 2018, issued to International Application No. PCT/IB2017/058227.

*Primary Examiner* — John R Downey
(74) *Attorney, Agent, or Firm* — Stein IP, LLC

(57) ABSTRACT

An ingestible capsule arranged, in use, to cross a human stomach for carrying out a phototherapeutic treatment arranged to combat an infection due to the presence of the bacterium *Helicobacter pylori*, the ingestible capsule comprising at least one primary light source arranged to emit an electromagnetic phototherapeutic wave having a wavelength $\lambda_1$, at least one auxiliary light source arranged to emit an electromagnetic phototherapeutic wave having a wavelength $\lambda_2$, a wrapper arranged to contain the or each primary light source and the or each auxiliary light source, the wrapper being at least partially transparent to the wavelengths $\lambda_1$, and $\lambda_2$, a control unit arranged to selectively activate the or each primary light source and/or the or each auxiliary light source.

6 Claims, 4 Drawing Sheets

(52) U.S. Cl.
CPC ............... *A61N 2005/0627* (2013.01); *A61N 2005/0652* (2013.01); *A61N 2005/0663* (2013.01)

(58) Field of Classification Search
CPC .... A61N 2005/0627; A61N 2005/0652; A61N 2005/0663
USPC .................................................... 607/88, 92
See application file for complete search history.

(56) References Cited

U.S. PATENT DOCUMENTS

| | | | |
|---|---|---|---|
| 2003/0223036 A1* | 12/2003 | Anderson | A61B 3/066 351/205 |
| 2004/0039242 A1* | 2/2004 | Tolkoff | A61N 5/0624 600/9 |
| 2008/0161748 A1 | 7/2008 | Tolkoff et al. | 604/21 |
| 2009/0177033 A1* | 7/2009 | Hendriks | A61B 1/0019 600/109 |
| 2012/0148976 A1* | 6/2012 | Brawn | A61N 5/0613 433/24 |
| 2012/0226335 A1* | 9/2012 | Surrenti | A61N 5/0624 607/89 |
| 2013/0053928 A1* | 2/2013 | Gat | A61B 5/0075 607/88 |
| 2014/0005758 A1* | 1/2014 | Ben-Yehuda | A61N 5/0613 607/92 |
| 2016/0151639 A1* | 6/2016 | Scharf | A61N 5/0601 607/92 |
| 2018/0140863 A1* | 5/2018 | Zapol | A61N 5/062 |

* cited by examiner

INGESTIBLE CAPSULE FOR THE PHOTOTHERAPEUTIC TREATMENT OF INFECTIONS

CROSS-REFERENCE TO RELATED APPLICATIONS

This application is a national stage of International Application No. PCT/IB2017/058227 filed Dec. 20, 2017, which claims the benefit of priority to Italian Application No. 102016000129679 filed Dec. 21, 2016, in the Italian Patent Office, the disclosures of which are incorporated herein by reference.

Field of the Invention

The present invention relates to the field of treatment of intestinal infections.

In particular, the invention relates to an ingestible capsule for phototherapeutic treatment of *Helicobacter pylori* infections.

Description of the Prior Art

As well known, *Helicobacter pylori* (*H. pylori*) is a Gram-negative microaerophilous bacterium that colonizes the mucus layer of the stomach and duodenum. The prevalence of infection is higher than 50% of the world population, up to 90% in developing countries. *H. pylori* can cause various diseases such as chronic gastritis, gastric and duodenal ulcers, gastric lymphoma, adenocarcinoma, and extra-digestive diseases. *H. pylori* is also considered a Class I carcinogen by the World Health Organization.

Currently, *H. pylori* infection is treated with a drug therapy that consists of a combination of a proton pump inhibitor with two or three antibiotics. Due to various side effects and antibiotic resistance, the efficacy of drug therapy is reduced to 70-85%.

To overcome these limitations, we use an approach based on a photodynamic therapy of the bacterium (PDT). PDT was introduced at the beginning of the last century and was originally used for the treatment of tumors. In traditional PDT, a non-toxic dye, called an external photosensitizer, is injected or applied by topical administration to the patient, being selectively accumulated in the target (i.e., a malignant tissue or bacterium). After about 48-72 hours, the lens is exposed to visible light. The interaction between the photosensitizer and the light, in the presence of oxygen, causes reactive oxygen species to be produced, inducing cell death. Applications of PDT to kill pathogenic microorganisms have met the increasing attention of clinicians, and this system has been proposed as a therapy for a wide variety of localized infections.

The recent return of interest to PDT has been largely driven by unstoppable growth in drug resistance, including many classes of pathogens. *H. pylori*, for example, is known to be photo-labile without the exogenous intake of photosensitizers. *H. pylori*, in fact, naturally possesses photoactive porphyrins, coproporphyrin and protoporphyrin IX, which are natural photosensitizers. For this reason, *H. pylori* can be killed by exposing it to light with appropriate wavelengths.

WO2011055395 describes an ingestible capsule for the specific phototherapy of *H. pylori* infections, in which the presence of at least a semiriflexing mirror is provided for increasing the illumination provided by the therapeutic light source.

However, this solution is not very efficient, since it is not adaptable to the different areas of the stomach, and therefore to the different stages of the infection caused by the *H. pylori* bacterium. Therefore, using this device, the patient should take more than one capsule, each suitable for a different area of the stomach, increasing the costs of therapy and making it more complex to implement for an untrained user.

WO2012123939A1 describes an ingestible capsule for the phototherapy of the gastrointestinal tract of a patient, in which the presence of one or more phototherapeutic light sources and a control unit suitable for activating the light sources is provided in order to administer a specific dose of therapeutic illumination in the gastrointestinal tract. The described capsule therefore allows a more adaptable administration to different areas of the gastrointestinal tract.

However this solution, not having as target specific the infection from *H. pylori*, is not much effective in the support to this particular therapy for which are necessary wavelength and methods of administration not provided by WO2012123939A1.

In particular, although the efficacy of some wavelengths for killing the bacterium in vitro has been demonstrated (M. R. Hamblin, J. Viveiros, C. Yang, A. Ahmadi, R. A. Ganz, and M. J., Tolkoff "*Helicobacter pylori* accumulates photoactive porphyrins and is killed by visible light," *Antimicrobial Acing Chemother.*, vol. 49, no. 7, pp. 2822-2827, July 2005) it should be considered that in vivo the bacterium is distributed differently and generally in a more complex way. It must therefore be considered that the bacterium must be treated in vivo within a human stomach, in which other factors are fundamental, among which for example the depth of penetration of light at different wavelengths. The gastric wall in fact, consisting of macroscopic structures (folds) and microscopic structures (pits), is a completely different situation respect to that one in which the bacterium is illuminated on a Petri dish under in vitro conditions. Folds and pits are characterized by lateral dimensions of the order respectively 2-4 mm and 100-200 µm, in which the bacterium can nestle and hide. In general, bactericidal efficiency in a real stomach is a multiparametric problem, whose parameters are represented both by the optical properties of the endogenous photosensitizer and by the photophysical properties of the stomach (absorption spectrum and ROS production efficiency) and by the optical properties of the tissue, which can strongly influence the spectrum of effective wavelengths for killing the bacterium. Considering the optical parameters of each layer of the gastric mucosa, it follows that the filtering action woven on certain wavelengths must be taken into account to optimize the effectiveness of photo-killing.

In order to optimize the efficacy of phototherapy by a small, ingestible device, the choice of the best emission wavelengths for the endoscopic capsule is essential to have a good eradication of the bacterium. The choice of the best spectral irradiation band is essential to obtain an effective photo-killing action and optimized energy management, without spending it in photons at different wavelengths from the most efficient one, also allowing to reduce the number of therapeutic sessions which, in this case, are translated with the effective reduction of the number of capsules necessary for the treatment. The use of specific and non-random wavelengths, allows to increase more than 50% the therapeutic efficacy of the single device without wasting energy in photons that are not useful for phototherapy of the specific bacterium.

Moreover, considering that the distribution of the bacterium inside the stomach is certainly dynamic and subject to variability in relation to the state of the infection, a dynamic selection of the wavelengths to be used is fundamental. It is known, for example, that *H. pylori*, although having adaptation systems that allow it to survive the acidic environment of the stomach, prefers an environment where the pH is higher. So it is possible to state that in an acute colonization phase the *H. pylori* is found exclusively in the antrum. As the infection continues, however, and you get to the chronic phase of gastritis or for the use of antacids eg, the bacterium tends to position itself in the highest parts of the stomach up to the body. In the most long-infected areas (antrum) the bacterium is located more deeply in depth, while in the areas of the body and the bottom the bacterium is more localized on the surface.

Not considering the aspects described above, both documents cited are not very effective in the treatment of *H. pylori*.

SUMMARY OF THE INVENTION

It is therefore a feature of the present invention to provide an ingestible capsule for the phototherapeutic treatment of *Helicobacter pylori* infections that allows a targeted and effective therapy, so as to reduce the number of capsules to be taken.

It is also a feature of the present invention to provide an ingestible capsule for the phototherapeutic treatment of *Helicobacter pylori* infections which allows to adapt in real time to the different areas of the stomach to be treated and to the different conditions to which the bacterium may be located.

It is still a feature of the present invention to provide an ingestible capsule for the phototherapeutic treatment of *Helicobacter pylori* infections which allows an optimized energy consumption with respect to the prior art capsules, so as to extend the therapeutic effect of each capsule.

These and other objects are achieved by an ingestible capsule arranged, in use, to cross a human stomach for carrying out a phototherapeutic treatment arranged to combat an infection due to the presence of the bacterium *Helicobacter pylori*, said ingestible capsule comprising:
- at least one primary light source arranged to emit an electromagnetic phototherapeutic wave having a wavelength $\lambda_1$;
- at least one auxiliary light source arranged to emit an electromagnetic phototherapeutic wave having a wavelength $\lambda_2$;
- a wrapper arranged to contain said or each primary light source and said or each auxiliary light source, said wrapper being at least partially transparent to said wavelengths $\lambda_1$ and $\lambda_2$;
- a control unit arranged to selectively activate said or each primary light source and/or said or each auxiliary light source;
- at least one energy source arranged to provide energy for feeding said control unit and/or said light sources;
- said wavelength $\lambda_1$ and $\lambda_2$ being such that 400 nm<$\lambda_1$<525 nm and 525 nm<$\lambda_2$<650 nm;
- whose main feature is that said control unit is also arranged to:
  - receive an information of position reporting in real time an area of said stomach crossed by said ingestible capsule;
  - on the basis of said information of position, determine a wavelength, a dosage and a duration of administration of said electromagnetic phototherapeutic waves for each light source in order to obtain a desired combination of the wavelengths $\lambda_1$ and $\lambda_2$ and therefore achieve an optimal phototherapeutic treatment of said area of said stomach;
  - selectively activate said or each primary light source and/or said or each auxiliary light source to provide said optimal phototherapeutic treatment of said area of said stomach.

The advantage with respect to the prior art is that it is possible to activate more phototherapeutic frequencies and manage their administration more effectively, maximizing the number of released photons (J/cm$^2$), without the need to insert more capsules into the stomach.

Advantageously, $\lambda_2 \cong 625$ nm and $\lambda_1 \cong 500$ nm.

More specifically, in a first step, in the body-bottom area of the stomach, it is possible to activate the light sources in such a way that the radiation emitted is for 20% composed of $\lambda_1 \cong 500$ nm and for 80% composed of $\lambda_2 \cong 625$ nm, in order to obtain a more effective and less penetrating radiation (around the blue/green) to treat the bacteria arranged on the surface.

In a second phase, while the capsule arrives in the antral area in the stomach, the proportion can instead gradually be varied, until it is inverted, arriving at a radiation composed for 80% of $\lambda_1 \cong 500$ nm and for 20% of $\lambda_2 \cong 625$ nm, so you can penetrate more into the mucus or between the folds of the stomach.

Advantageously, said control unit is also arranged to receive an information concerning the temperature of said light sources, said information concerning the temperature allowing to determine the duration of administration of said electromagnetic phototherapeutic waves to allow a lower consumption of the energy supplied by said energy source.

In particular, knowing the temperature of the light sources, the control unit can activate and deactivate the sources in order to optimize the ratio between emitted radiation and dispersed energy. It is in fact known that the working temperature influences the luminous efficiency of the LEDs (relative luminous efficiency of 100% at 20° C., of 80% at 40° C., of 60% at 60° C. for some types of LEDs, and this varies in function of the wavelength and the type of source used).

If, for example, the working temperature rises too much, the luminous efficiency may be negatively affected, and therefore it may be more convenient to switch the sources on and off, rather than keeping them on permanently. In this way the average luminous efficiency (the photons irradiated in the time unit) would become almost constant and in any case greater than in a situation in the absence of control. In this way, there would be a further improvement in the performance in terms of therapeutic efficacy of the single device, considering that the dynamic selection of wavelengths, driven by the operating temperature of the device and its position, allows an improvement in therapeutic efficacy of individual light sources. Always to reduce the temperature of the light sources, and increase the energy efficiency, the control unit, depending on the temperature sensor, may decide to turn off some LEDs unused at that time.

Advantageously, a detector of pH is also provided configured to measure the level of pH in the environment surrounding said ingestible capsule to provide said information of position to said control unit.

In particular, a more acidic environment will suggest that the capsule is in the antrum, while a less acidic environment will suggest that the capsule in the cecum.

Some reference values of the pH are the following:
esophagus pH=5-6 fundus pH=4-5
body of stomach pH=3-4
antrum pH=1-2
duodenum pH=7-8

In particular, an inertial sensor is also provided arranged to determine linear and angular speed and acceleration of said ingestible capsule to provide said information of position to said control unit.

The dynamic selection of wavelengths and their optimized management of ignition by the control unit could also be based on the positioning of the capsule or on its speed. Likewise, in some cases, it may select some wavelengths and some LEDs with lower intensity (for example in the final stages of therapy, when the capsule is about to cross the stomach and therefore is certainly in antral position where the lumen is restricted and there is no need to dose the light).

On the basis of the information coming from the inertial sensors, moreover, which show the path made by the capsule and its spatial orientation, it will also be possible to select the number and type of sources to be activated and the relative administration doses (which may be reduced in the case of stationing of the capsule at one point). In this way, it is possible to know both the path made by the capsule and its spatial orientation. From the position the control unit can determine the doses of administration, while depending on the orientation can select which sources to activate.

In particular, at least one magnetic sensor is also provided configured to measure a magnetic signal out of said stomach to provide said information of position to said control unit. In this way, by placing magnets/electromagnets in predetermined positions outside the user's body, the magnetic sensor allows to establish the position of the capsule on the basis of the intensity and direction of the magnetic signal.

Advantageously, at least one proximity sensor is also provided configured to measure the proximity of a wall of said stomach from said ingestible capsule. This way, if the capsule is attached to the wall, the control unit can turn off the light sources opposite to it.

By combining the localization information coming from the magnetic sensor and the orientation information coming from the proximity sensor, it is therefore possible to establish whether it is convenient to switch the LEDs on or off in a particular area of the capsule with respect to others.

Advantageously, said or each primary light source and said or each auxiliary light source are put in said transparent wrapper.

In particular, said or each primary light source and said or each auxiliary light source comprise organic and flexible diodes.

Advantageously, within said transparent wrapper a diffusive fluid is provided arranged to increase the diffusion of said light sources. In this way, the maximum angular coverage of the light radiation around the capsule is possible.

Furthermore, said transparent wrapper can comprise light guides arranged to convey said electromagnetic phototherapeutic waves along predetermined trajectories.

Advantageously, a ferromagnetic and/or magnetic element is also provided for allowing a guide of said ingestible capsule in said stomach by means of a magnet or an electromagnet external to said stomach. The ferromagnetic element may also be the battery itself, if there is one is inside the capsule.

In particular, a device for receiving energy by wireless transmission is provided. It can be, for example, a winding used also as an electromagnet for remote driving by means of a magnet.

In particular, the primary energy source for the capsule can be a battery located inside the capsule itself.

To this a winding system can be added or replaced with the aim of supplying energy to the capsule remotely. One possibility could be to guide the capsule, through a magnetic system or with an external electromagnet, at a specific point to maximize the transfer of energy in a continuous or not, to allow the same capsule to continue to carry out therapy for along time higher than the average time spent in the stomach.

In this way, thanks to the present invention, a single device is able to irradiate when necessary and in a variable manner with respect to the wavelengths selected and identified by the control unit, as is the case with the active ingredient management in drugs. The device makes it possible to irradiate the same point of the stomach with light of different colours specially selected overcoming the problem of random movements of the stomach that would otherwise not allow proper lighting of some gastric areas, reducing the effectiveness of the treatment.

In particular, a therapy combined with selected wavelengths allows:
immediate action concerning the reduction of the number of capsules that the patient must take, then a reduction of the risks associated with each capsule;
the possibility of composing in a controlled manner the advantages of all the wavelengths used, making it possible to achieve the best possible compromise in the future with regard to photodynamic therapy through a capsule.

In addition, given the presence of a control unit, the capsule is able to release a "variable dose combination" in relation to a multiparametric analysis with respect to the elapsed time, to the is variation of pH, to the presence of external magnetic fields, based on proximity sensors, and accelerometers, for optimal management of the energy source.

BRIEF DESCRIPTION OF THE DRAWINGS

Further characteristic and/or advantages of the present invention are more bright with the following description of an exemplary embodiment thereof, exemplifying but not limitative, with reference to the attached drawings in which.

DESCRIPTION OF A PREFERRED EXEMPLARY EMBODIMENT

Figure 1:
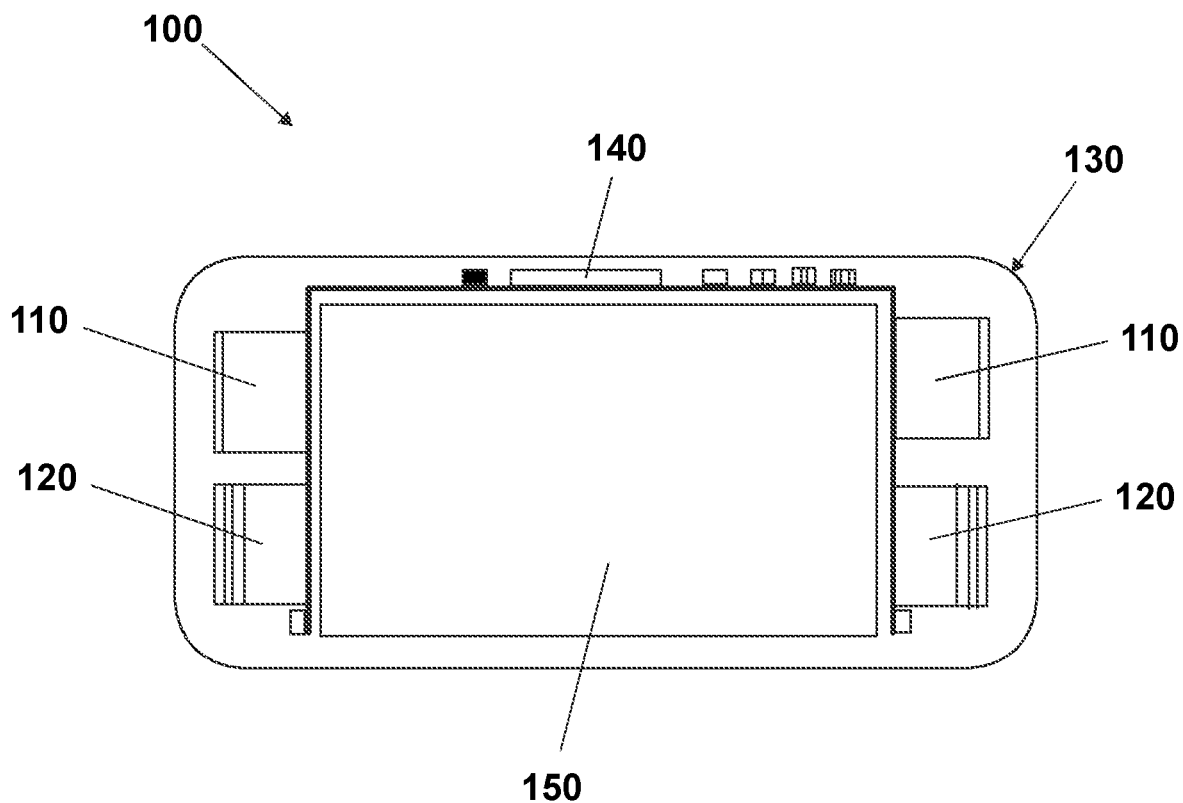
FIG. 1 shows a first exemplary embodiment of the ingestible capsule, according to the present invention, wherein 4 light sources are provided.

With reference to FIG. 1, in a first exemplary embodiment, the ingestible capsule 100, according to the present invention, comprises two primary light sources 110 arranged to emit an electromagnetic phototherapeutic wave having a wavelength $\lambda_1$ and two auxiliary light sources 120 arranged to emit an electromagnetic phototherapeutic wave having a wavelength $\lambda_2$. The ingestible capsule 100 then comprises a wrapper 130 at least partially transparent to the wavelengths $\lambda_1$ and $\lambda_2$ and arranged to contain the light sources 110 and 120. They are also present a control unit 140, arranged to selectively activate the light sources 110 and 120, and an energy source 150 arranged to provide energy for feeding the control unit 140 and the light sources 110 and 120.

Figure 2:
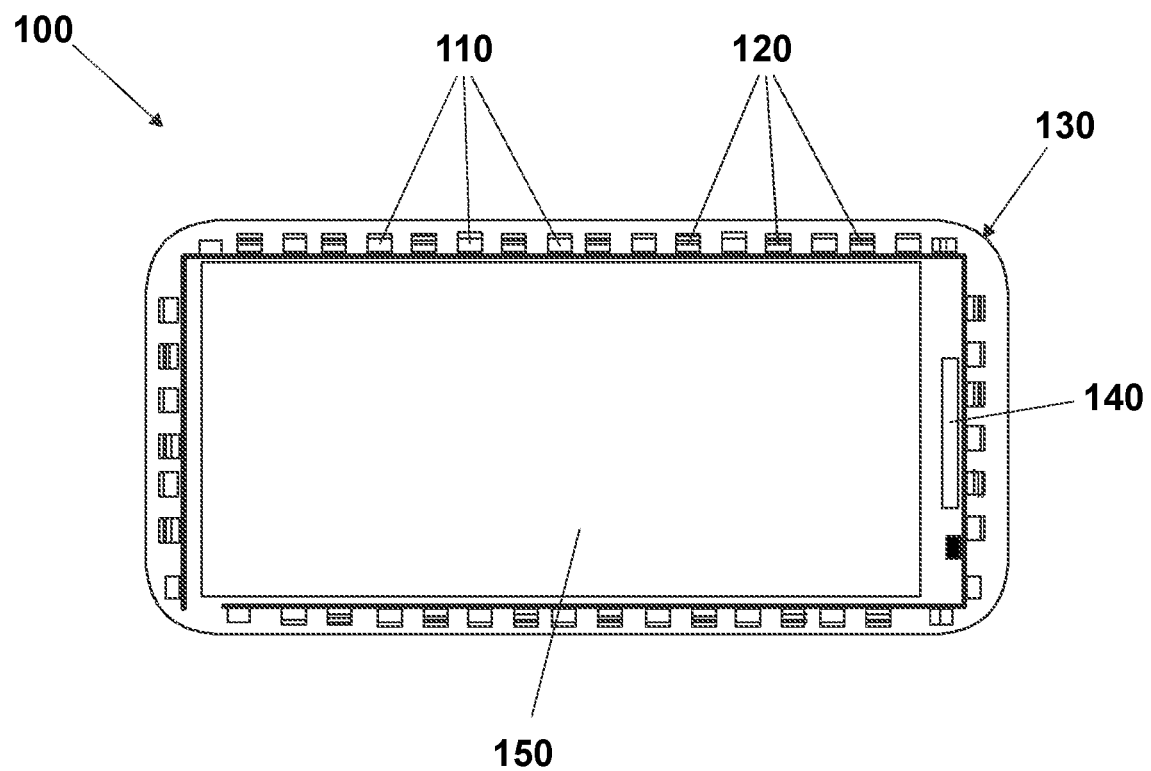
FIG. 2 shows a second exemplary embodiment of the ingestible capsule, according to the present invention, wherein a plurality of light sources is provided.
Figure 3A:
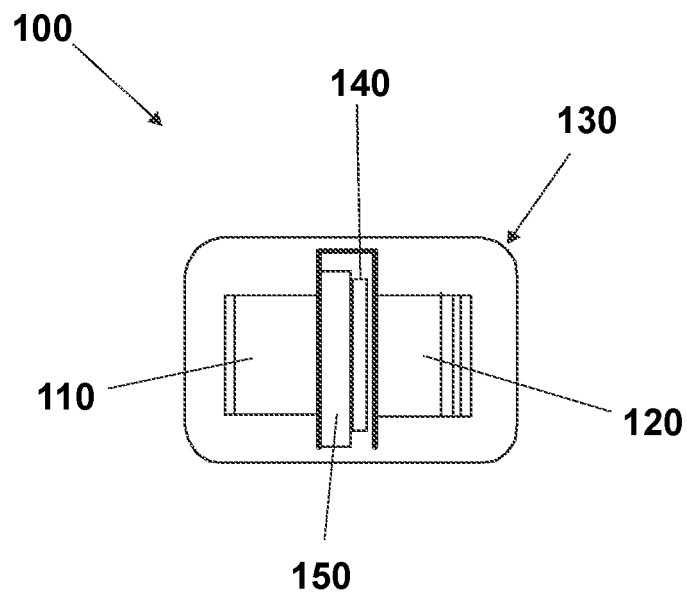
FIGS. 3A, 3B, 3C and 3D show other exemplary embodiments of the ingestible capsule having different forms and dispositions of the components.
Figure 3B:
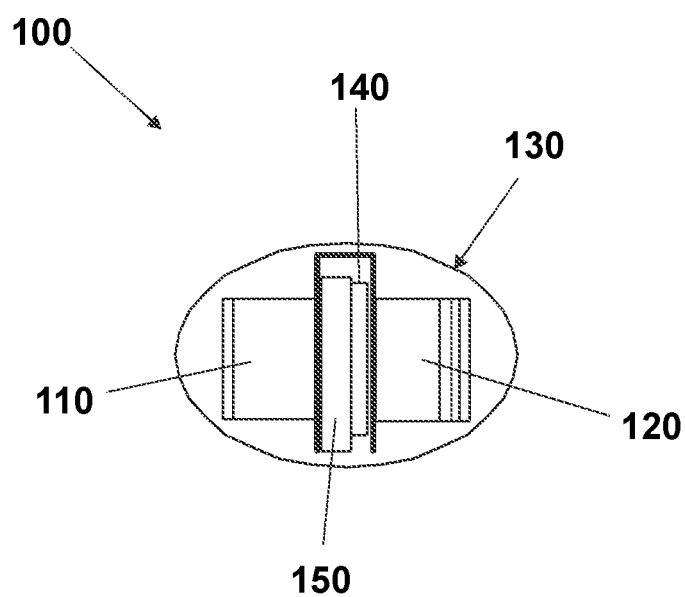
Figure 3C:
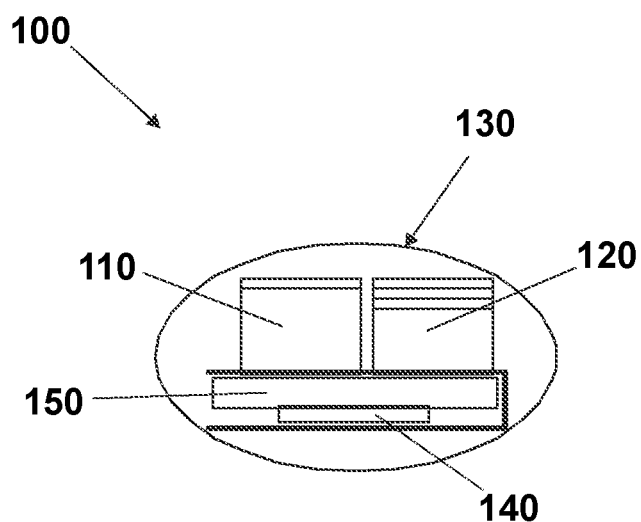
Figure 3D:
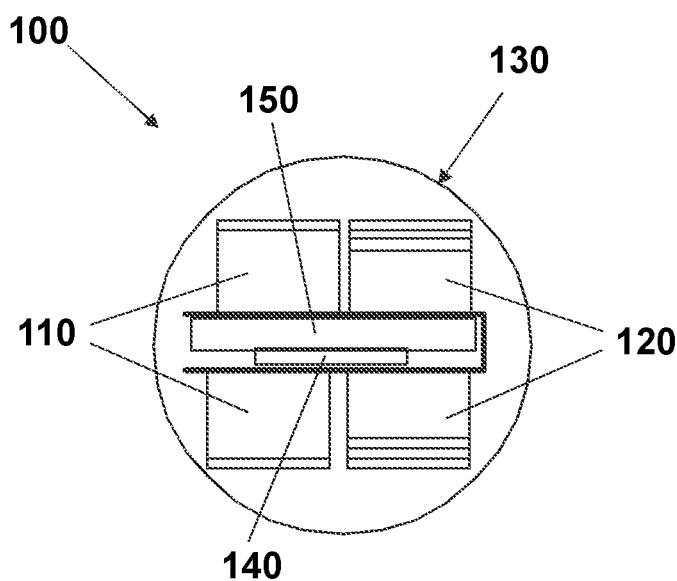

In FIG. 2 a second exemplary embodiment is shown in which there is a plurality of light sources 110 and 120 alternate to each other along all the perimeter of the capsule. This way, it is very increased the probability that the capsule 100, independently of its position and its orientation inside the stomach, can emit effective light waves, i.e. that reach the desired target for therapy.

In the FIGS. 3A, 3B, 3C and 3D some exemplary embodiments of the capsule are shown that have different forms of the wrapper 130 and, therefore, different dispositions of the inner components.

The foregoing description some exemplary specific embodiments will so fully reveal the invention according to the conceptual point of view, so that others, by applying current knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realise the different functions described herein could have a different nature without, for this reason, departing from the field of the invention, it is to be understood that the phraseology or terminology that is employed herein is for the purpose of description and not of limitation.

The invention claimed is:

1. An ingestible capsule arranged, in use, to cross a human stomach for carrying out a phototherapeutic treatment arranged to combat an infection due to the presence of the bacterium *Helicobacter pylori*, said ingestible capsule comprising:
   at least one primary light source arranged to emit an electromagnetic phototherapeutic wave having a wavelength $\lambda_1$;
   at least one auxiliary light source arranged to emit an electromagnetic phototherapeutic wave having a wavelength $\lambda_2$;
   a wrapper arranged to contain said or each primary light source and said or each auxiliary light source, said wrapper being at least partially transparent to said wavelengths $\lambda_1$ and $\lambda_2$;
   a control unit arranged to selectively activate said or each primary light source and/or said or each auxiliary light source;
   at least one energy source arranged to provide energy for feeding said control unit and/or said light sources;
   a detector of pH configured to measure a level of pH in an environment surrounding said ingestible capsule to provide a first information of position of said ingestible capsule to said control unit;
   an inertial sensor arranged to determine linear and angular speed and acceleration of said ingestible capsule to provide a second information of position of said ingestible capsule to said control unit;
   said wavelength $\lambda_1$ and $\lambda_2$ being such that 400 nm<$\lambda_1$<525 nm and 525 nm<$\lambda_2$<650 nm;
   said control unit is also arranged to:
      receive said first information of position from said detector of pH and said second information of position from said inertial sensor;
      process said first and second information of position to provide a real-time estimate of an area of said stomach crossed by said ingestible capsule;
         on the basis of said real-time estimate, determine a wavelength, a dosage and a duration of administration of said electromagnetic phototherapeutic waves for each light source in order to obtain a desired combination of said wavelengths $\lambda_1$ and $\lambda_2$ and therefore achieve an optimal phototherapeutic treatment of said area of said stomach;
         selectively activate said or each primary light source and/or said or each auxiliary light source to provide said optimal phototherapeutic treatment of said area of said stomach.

2. The ingestible capsule, according to claim 1, wherein $\lambda_2 \cong 625$ nm and $\lambda_2 \cong 500$ nm.

3. The ingestible capsule, according to claim 1, wherein said control unit is also arranged to receive an information concerning the temperature of said light sources, said information concerning the temperature allowing to determine the duration of administration of said electromagnetic phototherapeutic waves to allow a lower consumption of the energy supplied by said energy source.

4. The ingestible capsule, according to claim 1, wherein at least one proximity sensor is also provided configured to measure the proximity of a wall of said stomach from said ingestible capsule.

5. The ingestible capsule, according to claim 1, wherein within said transparent wrapper a diffusive fluid is provided arranged to increase the diffusion of said light sources.

6. The ingestible capsule, according to claim 1, wherein said transparent wrapper comprises light guides arranged to convey said electromagnetic phototherapeutic waves along predetermined trajectories.

* * * * *